United States Patent
Dhanasingh et al.

(10) Patent No.: US 10,870,001 B2
(45) Date of Patent: Dec. 22, 2020

(54) ELECTRODE CONTACT WITH HYDROGEL COVERING

(71) Applicant: MED-EL Elektromedizinische Geraete GmbH, Innsbruck (AT)

(72) Inventors: Anandhan Dhanasingh, Innsbruck (AT); Claude Jolly, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 293 days.

(21) Appl. No.: 14/915,653

(22) PCT Filed: Sep. 4, 2014

(86) PCT No.: PCT/US2014/053987
§ 371 (c)(1),
(2) Date: Mar. 1, 2016

(87) PCT Pub. No.: WO2015/034981
PCT Pub. Date: Mar. 12, 2015

(65) Prior Publication Data
US 2016/0213913 A1    Jul. 28, 2016

Related U.S. Application Data
(60) Provisional application No. 61/874,388, filed on Sep. 6, 2013.

(51) Int. Cl.
*A61N 1/05* (2006.01)
(52) U.S. Cl.
CPC ................. *A61N 1/0541* (2013.01)

(58) Field of Classification Search
CPC .. A61N 1/0541; A61N 1/36032; A61N 1/375; H04R 25/606; H04R 25/70; H04R 25/48
USPC .......................................... 607/137
See application file for complete search history.

(56) References Cited

U.S. PATENT DOCUMENTS

| | | | |
|---|---|---|---|
| 4,658,835 A | 4/1987 | Pohndorf | |
| 5,786,439 A * | 7/1998 | Van Antwerp | A61B 5/14865 427/2.12 |
| 7,519,435 B2 | 4/2009 | Parker et al. | |
| 8,190,271 B2 | 5/2012 | Overstreet et al. | |
| 2007/0060815 A1 | 3/2007 | Martin et al. | |
| 2008/0103576 A1 * | 5/2008 | Gerber | A61N 1/0534 607/128 |

(Continued)

OTHER PUBLICATIONS

International Searching Authority, International Search Report and Written Opinion for PCT/US14/53987, dated Jan. 22, 2015, 21 pages.

*Primary Examiner* — Mallika D Fairchild
*Assistant Examiner* — Minh Duc G Pham
(74) *Attorney, Agent, or Firm* — Sunstein LLP

(57) ABSTRACT

A cochlear implant electrode includes an implantable electrode array made of resilient material with a center longitudinal axis and an outer surface. Electrode contacts are distributed on the outer surface of the electrode array along the longitudinal axis for applying electrical stimulation signals to adjacent neural tissue. At least one biocompatible hydrogel layer is fixed to the electrode array solely by mechanical connection and adapted to swell from contact with perilymph fluid within a cochlea without separating away from the outer surface of the electrode array.

11 Claims, 4 Drawing Sheets

(56) References Cited

U.S. PATENT DOCUMENTS

| | | | | |
|---|---|---|---|---|
| 2008/0103579 A1* | 5/2008 | Gerber | ............... | A61N 1/0558 |
| | | | | 607/149 |
| 2010/0121422 A1* | 5/2010 | Jolly | ................. | A61K 9/0024 |
| | | | | 607/137 |
| 2011/0034969 A1* | 2/2011 | Capcelea | ............ | B82Y 15/00 |
| | | | | 607/57 |
| 2011/0178587 A1* | 7/2011 | Chambers | .......... | A61N 1/0541 |
| | | | | 607/137 |

* cited by examiner

ELECTRODE CONTACT WITH HYDROGEL COVERING

This application is a National Phase Entry of Patent Cooperation Treaty Application PCT/US2014/053987, filed Sep. 4, 2014, which in turn claims priority from U.S. Provisional Patent Application 61/874,388, filed Sep. 6, 2013, both of which are incorporated herein by reference in their entireties.

FIELD OF THE INVENTION

The present invention relates to implantable electrodes for medical devices and specifically to mechanical fixation of a hydrogel covering over the electrode contacts.

BACKGROUND ART

A normal ear transmits sounds as shown in FIG. 1 through the outer ear 101 to the tympanic membrane 102 which moves the bones of the middle ear 103 that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode can electrically stimulate auditory nerve tissue with small currents delivered by multiple electrode contacts distributed along the electrode.

FIG. 1 also shows some components of a typical cochlear implant system where an external microphone provides an audio signal input to an external signal processor 111 in which various signal processing schemes can be implemented. The processed signal is then converted into a digital data format for transmission by external transmitter coil 107 into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrode contacts 112 on its surface that provide selective stimulation of the cochlea 104.

After an electrode array has been implanted, the body can react by forming fibrous tissue around the array. This adversely affects the impedance and charge transfer from the electrode contacts, and thus should be avoided or minimized. One way to do that is to form a layer of hydrogel material over the electrode contacts. Such hydrogel material is biocompatible and electrically conductive so as to allow for the intended charge transfer from the electrode contact to the adjacent tissue. But the hydrogel material also prevents the direct contact of the metal material of the electrode contacts (e.g., platinum) with the cochlear tissue and thereby avoids formation of the undesirable fibrous tissues over the electrode contacts. See, for example, U.S. Pat. Nos. 5,786,439, 7,519,435, 7,519,435, 8,190,271; which are incorporated herein by reference.

The hydrogel materials swells when it contacts the perilymph fluid within the cochlea, absorbing more than its own dry weight. As this swelling occurs, polymer branches in the hydrogel matrix grow much larger, forcing the hydrogel material away from the electrode surface it lies against. The chemical bond that normally is used to connect the hydrogel material to the electrode array often is not strong enough to resist these swelling induced forces. When that happens, the hydrogel material separates from the electrode array and can undesirably wander away from the implanted array.

SUMMARY OF THE INVENTION

Embodiments of the present invention are directed to a cochlear implant electrode that includes an implantable electrode array made of resilient material with a center longitudinal axis and an outer surface. Electrode contacts are distributed on the outer surface of the electrode array along the longitudinal axis for applying electrical stimulation signals to adjacent neural tissue. At least one biocompatible hydrogel layer is fixed to the electrode array solely by mechanical connection and adapted to swell from contact with perilymph fluid within a cochlea without separating away from the outer surface of the electrode array.

There may be at least one fixation groove on the outer surface of the electrode array adapted to fixedly connect to a portion of the hydrogel layer for mechanically fixing the hydrogel layer to the electrode array. The fixation groove may be parallel or perpendicular to the center longitudinal axis. A portion of the fixation groove may be undercut to mechanically lock the portion of the hydrogel layer within the fixation groove. There may be multiple fixation grooves. In some embodiments, there may be at least two openings connected together through the interior of the electrode array and filled with hydrogel material of the hydrogel layer to mechanically connect the hydrogel layer to the electrode array.

There may be multiple hydrogel sleeves fitting around the outer surface of the electrode array over each of the electrode contacts. And there may be a polymer mesh over each hydrogel sleeve that is adapted to generate a compressive force on the hydrogel sleeve when it swells. In some embodiments, the hydrogel layer may be adapted to release a therapeutic drug over a prolonged treatment period.

DETAILED DESCRIPTION OF SPECIFIC EMBODIMENTS

Embodiments of the present invention are directed to an implant electrode for a medical implant system such as a cochlear implant system that includes a hydrogel layer over the electrode contacts that is mechanically fixed to the electrode array material. The mechanical fixation resists the separation of the hydrogel layer from the implant electrode. In some embodiments, the hydrogel layer may be adapted to also release a therapeutic drug over a prolonged treatment period.

Figure 1:
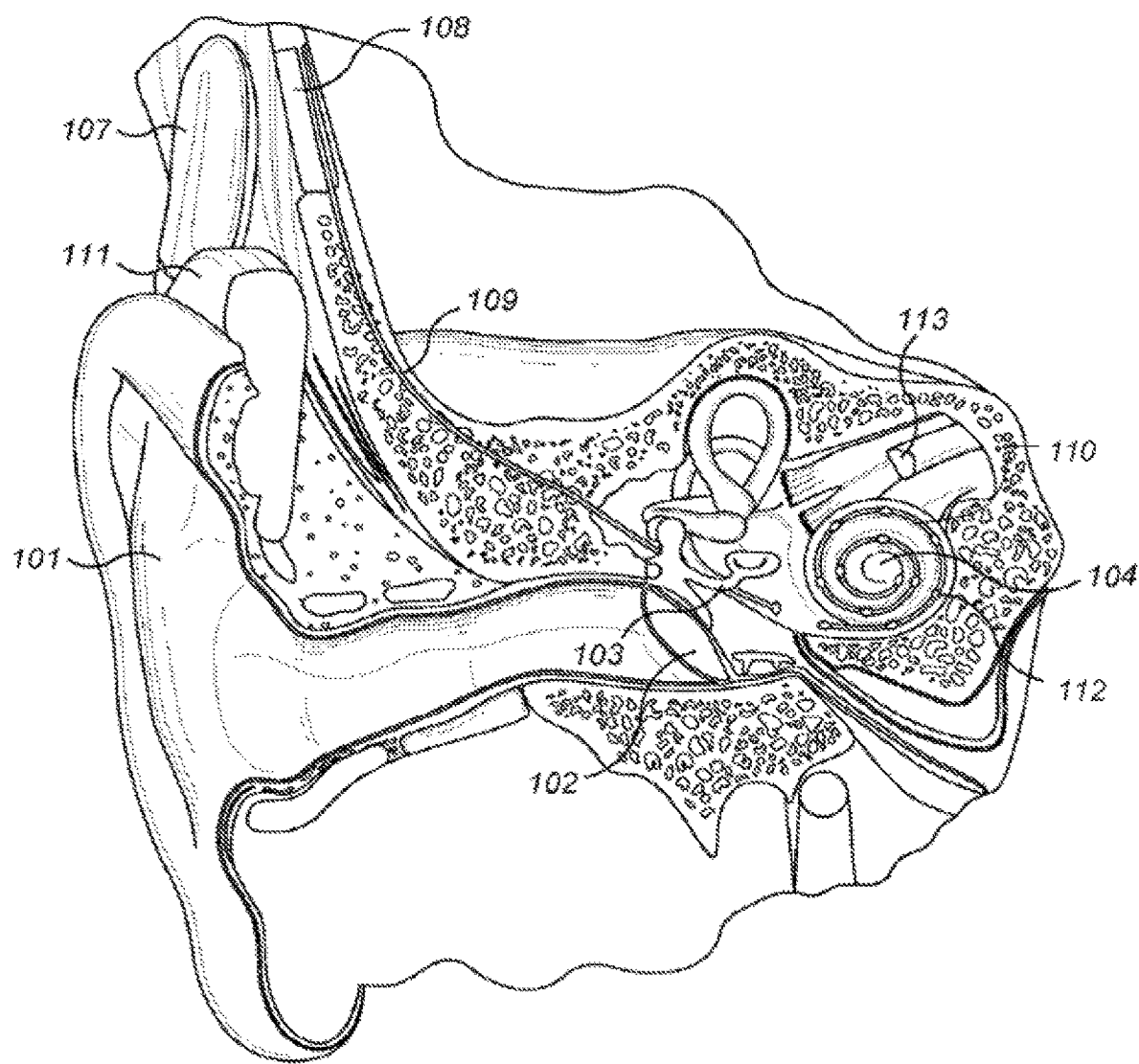
FIG. 1 shows the anatomy of the human ear with a cochlear implant system.
Figure 2A:
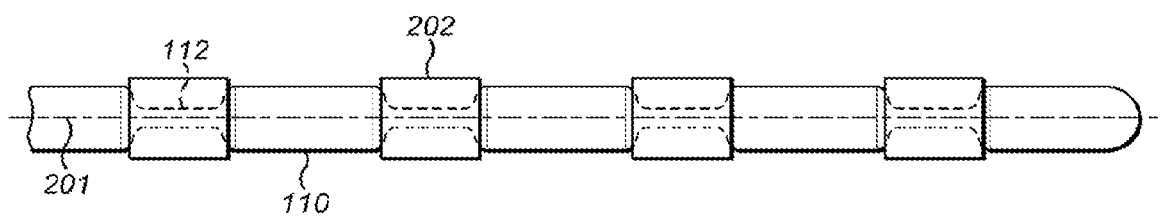
FIG. 2A-B shows a side view of the apical end of a cochlear implant electrode having hydrogel layers according to an embodiment of the present invention.
Figure 2B:
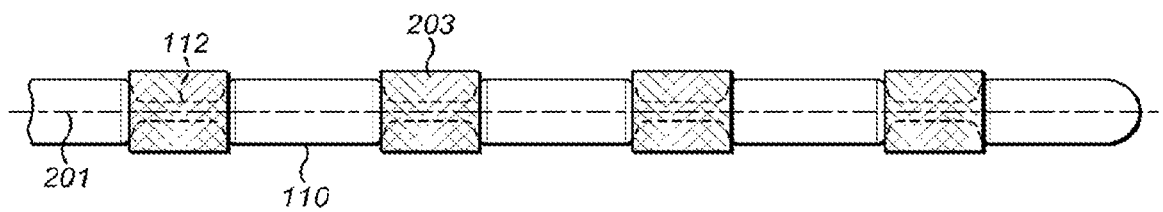

There are various different specific ways to mechanically fix the hydrogel layer to the implant electrode. FIG. 2A shows one approach where multiple electrically-conductive biocompatible hydrogel sleeves 202 fit tightly around the outer surface of the implantable electrode array 110 over each of the electrode contacts 112, which are distributed on the outer surface of the electrode array 110 along the center longitudinal axis 201 to apply the electrical stimulation signals to adjacent neural tissue within the cochlea 104. The hydrogel sleeves 202 fit tightly over each of the electrode contacts 112 perpendicularly to the longitudinal axis 201. During manufacturing, the hydrogel sleeves 202 are formed and pushed over the electrode array 110 to the desired position over each of the electrode contacts 112. When exposed to the perilymph fluid due to implantation in the cochlea, the hydrogel material swells. By choosing the geometry of the hydrogel sleeves 202 in the form of a closed loop, this swelling shrinks the inner diameter of the hydrogel sleeves 202 and thereby creates a compressive force that fixates onto the electrode array 110. The embodiment shown in FIG. 2B shows a further embodiment with the addition of a polymer mesh 203 over each hydrogel sleeve 202 that is adapted to generate a compressive force on the hydrogel sleeve 202 when it swells.

Figure 3A:
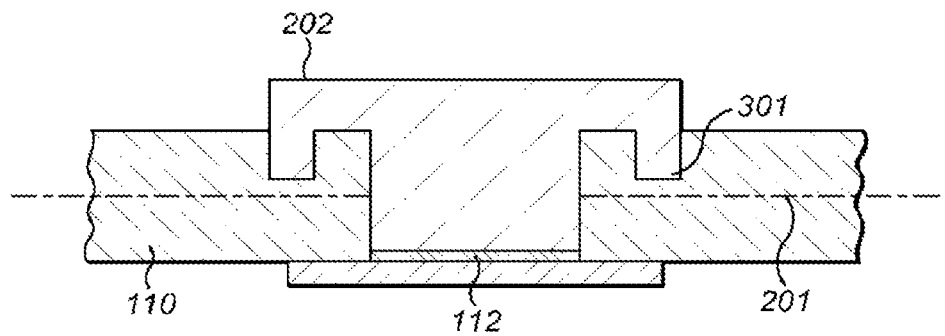
FIG. 3A-C shows a side view of a portion of a cochlear implant electrode having hydrogel layers according to embodiments of the present invention.
Figure 3B:
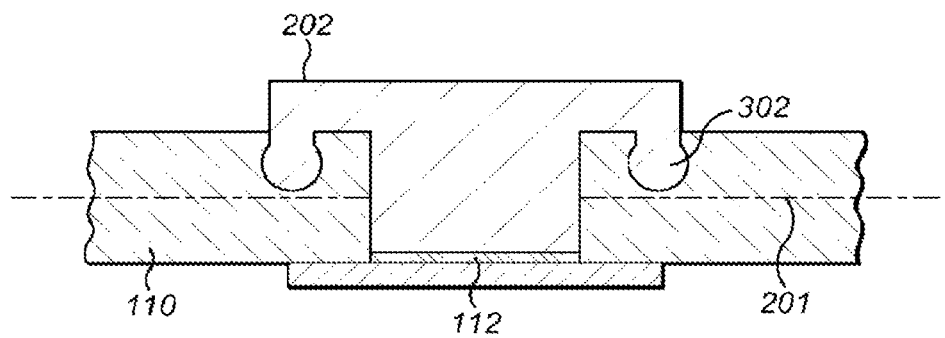
Figure 3C:
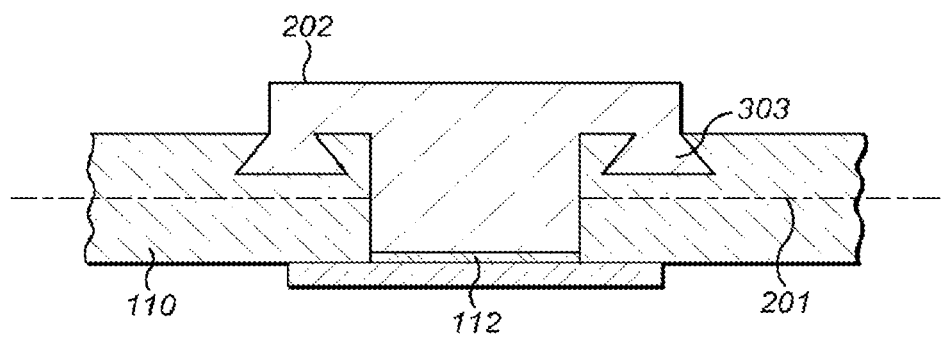

In addition or alternatively to the foregoing, there may be at least one fixation groove on the outer surface of the electrode array that is adapted to fixedly connect to a portion of the hydrogel layer for mechanically fixing the hydrogel layer to the electrode array. FIG. 3A-C shows a side view of a portion of an electrode array 110 having hydrogel sleeves 202 according to embodiments of the present invention which further include the addition of such fixation grooves in the electrode carrier material. Specifically, FIG. 3A shows the addition of fixation grooves 301 as two parallel channels around at least a portion of the electrode array 110 that are perpendicular to the center longitudinal axis 201 on either side of the electrode contact 112. The fixation grooves 301 further secure the hydrogel sleeve 202 in position over the electrode contact 112. During manufacturing, the dry hydrogel sleeve 202 is placed on the electrode array 110 such that part of the hydrogel body snugly fits and fills the fixation groove 301. Upon contact with perilymph fluid the hydrogel material swells, which causes the portion of the hydrogel sleeve 202 within the fixation groove 301 to also swell. This produces a compressive force that firmly fixes the hydrogel material in the fixation groove 301. The more the hydrogel swells, the greater the compressive force will be and the better the mechanical fixation will be. Consequently another resulting advantage is that different types of hydrogel material can be used and regardless of much swelling occurrence in response to fluid contact, the mechanical fixation always ensures that the hydrogel sleeve 202 will not separate from the electrode array 110.

In some such embodiments, a portion of the fixation groove may be undercut to further mechanically lock the portion of the hydrogel material within the fixation groove. FIG. 3B shows an example of an embodiment wherein the fixation groove 302 has a curved undercut, and FIG. 3C shows an example of an embodiment wherein the fixation groove 303 has a curved undercut.

Figure 4:
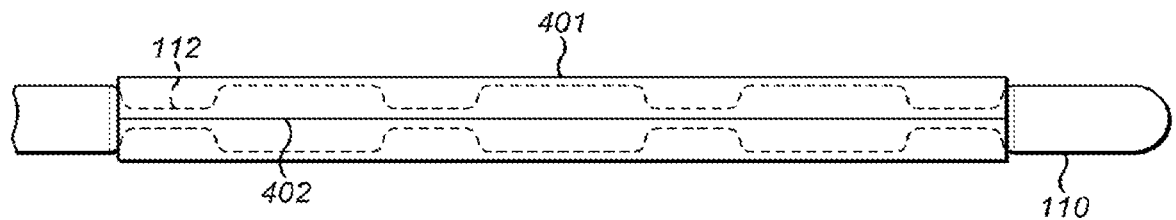
FIG. 4 shows a side view of the apical end of a cochlear implant electrode having a hydrogel layer according to an embodiment of the present invention.

FIG. 4 shows an example of another specific embodiment of the present invention where the electrode array 110 is covered by a single extensive hydrogel layer 401 that covers all of the electrode contacts 112 and which is mechanically fixed by a longitudinal fixation groove 402 along the length of the electrode array 110 parallel to the center longitudinal axis.

Figure 5:
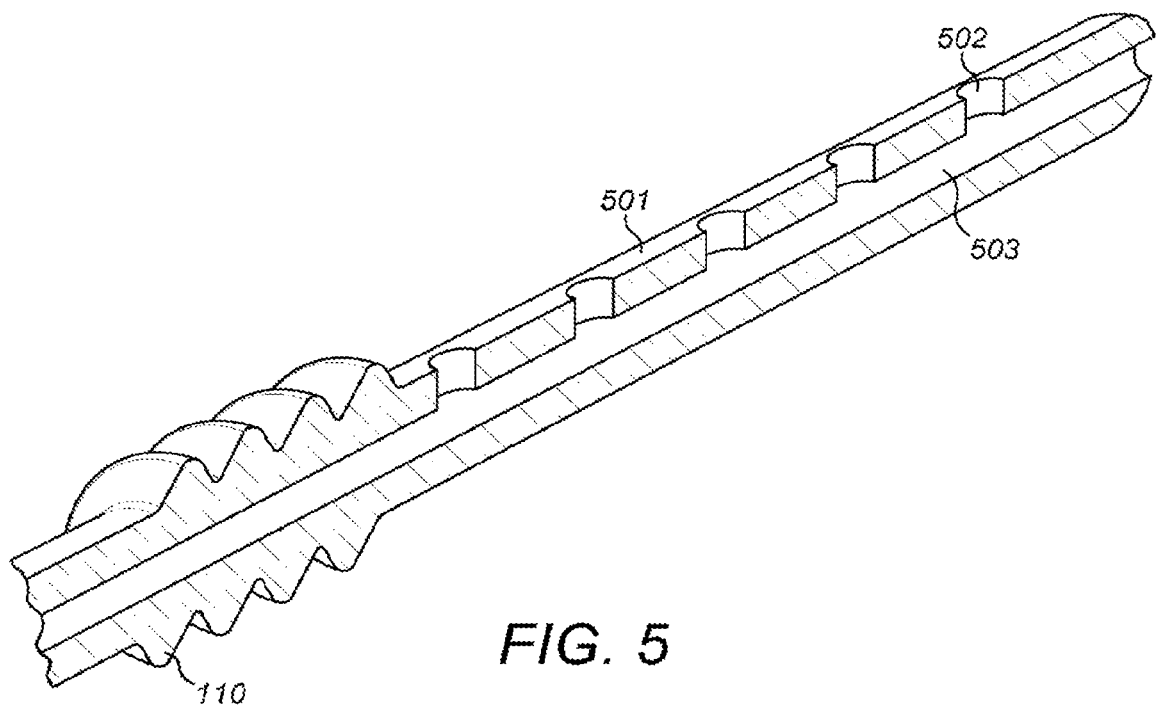
FIG. 5 shows a side cross-section of a cochlear implant electrode array having surface openings for mechanical fixation of the hydrogel layer.

FIG. 5 shows a side cross-section of a cochlear implant electrode array 110 having surface openings 502 for mechanical fixation of the hydrogel layer 501. There are at least two surface openings 502 that are connected together in an interior channel 503 of the electrode array 110. During manufacturing, the electrode array 110 can be immersed in a hydrogel solution which is sucked into the surface openings 502. After the hydrogel solution is polymerized, the hydrogel layer 501 covers the outer surface of the electrode array 110 and is mechanically connected to the electrode array 110 by the closed loop of the hydrogel material that forms between the interior channel 503 that connects the surface openings 502. This completely prevents the hydrogel layer 501 from separating from the surface of the electrode array 110, and with the swelling of the hydrogel material from the cochlear fluid, this mechanical fixation is further strengthened and there is no need of chemical bonds between the electrode array 110 and the hydrogel layer 501.

Although various exemplary embodiments of the invention have been disclosed, it should be apparent to those skilled in the art that various changes and modifications can be made which will achieve some of the advantages of the invention without departing from the true scope of the invention.

What is claimed is:

1. A cochlear implant electrode comprising:
    an implantable electrode array made of resilient material having a center longitudinal axis and an outer surface;
    a plurality of electrode contacts distributed on the outer surface of the electrode array along the longitudinal axis for applying electrical stimulation signals to adjacent neural tissue; and
    at least one biocompatible hydrogel layer fixed to the electrode array solely by mechanical connection and adapted to swell from contact with perilymph fluid within a cochlea without separating away from the outer surface of the electrode array;
    wherein the electrode array includes at least two openings connected together through the interior of the electrode array and filled with hydrogel material of the hydrogel layer to form a closed loop of hydrogel material to mechanically connect the hydrogel layer to the electrode array.

2. An electrode according to claim 1, further comprising:
    at least one fixation groove on the outer surface of the electrode array adapted to fixedly connect to a portion of the hydrogel layer for mechanically fixing the hydrogel layer to the electrode array.

3. An electrode according to claim 2, wherein a portion of the fixation groove is undercut to mechanically lock the portion of the hydrogel layer within the fixation groove.

4. An electrode according to claim 2, wherein there are a plurality of fixation grooves.

5. An electrode according to claim 2, wherein the at least one fixation groove is parallel to the center longitudinal axis.

6. An electrode according to claim 2, wherein the at least one fixation groove is perpendicular to the center longitudinal axis.

7. An electrode according to claim 6, wherein the at least one fixation groove includes two parallel channels perpendicular to the center longitudinal axis on either side of one electrode contact.

8. An electrode according to claim 1, wherein the hydrogel layer comprises a plurality of hydrogel sleeves fitting around the outer surface of the electrode array over each of the electrode contacts.

9. An electrode according to claim 8, further comprising:

a polymer mesh over each hydrogel sleeve adapted to generate a compressive force on the hydrogel sleeve when the hydrogel layer swells.

10. An electrode according to claim 1, wherein the hydrogel layer is adapted to release a therapeutic drug over a prolonged treatment period.

11. An electrode according to claim 1, wherein the at least one hydrogel layer fits around the outer surface of the electrode array over one or more of the electrode contacts and the electrode array includes the at least two openings connected together through the interior of the electrode array and filled with the hydrogel material to form the closed loop of the hydrogel material, one portion of the closed loop covering the one or more electrode contacts.

* * * * *